United States Patent [19]

Pollmann et al.

[11] Patent Number: 5,288,636

[45] Date of Patent: Feb. 22, 1994

[54] ENZYME ELECTRODE SYSTEM

[75] Inventors: Klaus H. Pollmann, Neulussheim, Fed. Rep. of Germany; Martin T. Gerber, Carmel; Kent M. Kost, Fishers; M. Luann Ochs, Fishers; P. Douglas Walling, Indianapolis; Joseph E. Bateson, Fishers; Lance S. Kuhn, Indianapolis; Chi-Neng A. Han, Indianapolis, all of Ind.

[73] Assignee: Boehringer Mannheim Corporation, Indianapolis, Ind.

[21] Appl. No.: 627,667

[22] Filed: Dec. 14, 1990

Related U.S. Application Data

[63] Continuation-in-part of Ser. No. 451,671, Dec. 15, 1989, abandoned.

[51] Int. Cl.$^5$ .......................... C12M 1/40; C12M 1/34
[52] U.S. Cl. .................................. 435/288; 435/291; 435/817; 204/403
[58] Field of Search ............... 435/4.14, 25, 288, 291, 435/817; 204/153.11, 153.17, 403, 415

[56] References Cited

U.S. PATENT DOCUMENTS

| 4,224,125 | 9/1980 | Nakamura et al. | 204/195 |
|---|---|---|---|
| 4,543,326 | 9/1985 | Miyashita et al. | 435/15 |
| 4,758,323 | 7/1988 | Davis et al. | 204/403 |
| 4,810,633 | 3/1989 | Bauer et al. | 435/28 |
| 4,820,399 | 4/1989 | Senda et al. | 435/9 |
| 4,830,959 | 5/1989 | McNeil et al. | 435/7 |
| 4,894,137 | 1/1990 | Takizawa et al. | 204/403 |
| 4,897,173 | 1/1990 | Nankai et al. | 204/403 |
| 4,959,305 | 9/1990 | Woodrum | 435/7 |
| 4,999,582 | 3/1991 | Parks et al. | 472/82.02 |

FOREIGN PATENT DOCUMENTS

| 0127958A2 | 12/1984 | European Pat. Off. | G01N 48 |
|---|---|---|---|
| 0136362A1 | 4/1985 | European Pat. Off. | G01N 30.46 |
| 0080304B1 | 5/1986 | European Pat. Off. | C12Q 26 |
| 0206218A2 | 12/1986 | European Pat. Off. | G01N 30 |
| 0230472A1 | 8/1987 | European Pat. Off. | G01N 30.46 |
| 0359831A1 | 3/1990 | European Pat. Off. | G01N 28.30 |

(List continued on next page.)

OTHER PUBLICATIONS

Talbott, Jonathan Lee, "Enzymatic Amperometry of Glucose", a Ph.D. Dissertation for The Pennsylvania State University, Graduate School Department of Chemistry, dated Jan. 1988.

Nankai, et al., Japanese Sensor Newsletter, vol. 3, No. 1, Mar. 1989-pp. 16-20, published by Edison Sensor Technology Center, Case Western Reserve University, Cleveland, Ohio.

Williams et al. "Electrochemical-Enzymatic Analysis . . . " Analytical Chem., vol. 42, No. 1 (Jan. 1970) pp. 118-121.

*Primary Examiner*—Michael G. Wityshyn
*Assistant Examiner*—William H. Beisner
*Attorney, Agent, or Firm*—D. Michael Young; Max J. Kenemore; Marilyn L. Amick

[57] ABSTRACT

A biosensor that includes working and counter electrodes of substantially the same size and made of the same electrically conducting material. A reagent is contained in a reagent well in the biosensor. The reagent includes a redox mediator, an enzyme, and a buffer, and covers substantially equal surface areas of portions of the working and counter electrodes. When a sample, containing the analyte to be measured, is added to the reagent well, a reaction occurs that oxidizes the analyte and reduces the redox mediator. After this reaction is complete, an electrical potential difference is applied between the electrodes. The amount of oxidized form of the redox mediator at the counter electrode and the applied potential difference must be sufficient to cause diffusion limited electrooxidation of the reduced form of the redox mediator at the surface of the working electrode. After a short time delay, current produced by the electrooxidation of the reduced form of the redox mediator is measured and the observed current is correlated to the amount of the analyte in the sample. In some cases, the analyte sought to be measured may be reduced and the redox mediator may be oxidized. In such cases, current produced by diffusion limited electroreduction of the oxidized form of the redox mediator is measured and correlated to the amount of analyte in the sample.

38 Claims, 2 Drawing Sheets

FOREIGN PATENT DOCUMENTS

| | | | |
|---|---|---|---|
| 0400918 | 12/1990 | European Pat. Off. | G01N 30.46 |
| 60-173457 | 9/1985 | Japan | G01N 46.30 |
| 60-173458 | 9/1985 | Japan | G01N 30.46 |
| 60-173459 | 9/1985 | Japan | G01N 46.30 |
| 61-90050 | 5/1986 | Japan | G01N 30.46 |
| 1091558 | 5/1986 | Japan | |
| 63-58149 | 3/1988 | Japan | G01N 46.30 |
| 63-128252 | 5/1988 | Japan | G01N 46.30 |
| 63-139246 | 6/1988 | Japan | G01N 30.46 |
| 63-317757 | 12/1988 | Japan | G01N 46.30 |
| 63-317758 | 12/1988 | Japan | G01N 30.28 |
| 64-23163 | 1/1989 | Japan | G01N 30.46 |
| 1-114746 | 5/1989 | Japan | G01N 46.30 |
| 1-114747 | 5/1989 | Japan | G01N 46.30 |
| 1-134244 | 5/1989 | Japan | G01N 30 |
| 1-156658 | 6/1989 | Japan | G01N 46 |
| WO89/08713 | 9/1989 | PCT Int'l Appl. | G01N 26 |
| 2154003B | 2/1988 | United Kingdom | G01N 28 |
| 2204408A | 11/1988 | United Kingdom | G01N 12.46 |

ENZYME ELECTRODE SYSTEM

CROSS-REFERENCES TO RELATED APPLICATIONS

This application is a continuation-in-part of U.S. patent application No. 07/451,671, filed Dec. 15, 1989, now abandoned.

FIELD OF THE INVENTION

This invention relates generally to the determination of the concentration of analytes in fluids and more specifically to an amperometric biosensor for use in such determinations.

BACKGROUND OF THE INVENTION

Biosensors are not new. Their use in the determination of concentrations of various analytes in fluids is also known.

Nankai et al , WO 86/07632, published Dec. 31, 1986, discloses an amperometric biosensor system in which a fluid containing glucose is contacted with glucose oxidase and potassium ferricyanide. The glucose is oxidized and the ferricyanide is reduced to ferrocyanide. (This reaction is catalyzed by glucose oxidase.) After two minutes, an electrical potential is applied and a current caused by the re-oxidation of the ferrocyanide to ferricyanide is obtained. The current value, obtained a few seconds after the potential is applied, correlates to the concentration of glucose in the fluid.

Because Nankai et al. discloses a method in which the reaction of glucose and ferricyanide may run to completion prior to the application of an electrical potential, this method is referred to as the "end-point" method of amperometric determination.

Nankai et al. discloses a system, wherein the glucose oxidase and potassium ferricyanide are held on a nonwoven nylon mesh. The mesh is positioned so that it is in contact with a working electrode, a counter electrode and a reference electrode. The total surface area of the counter and reference electrodes is twice that of the working electrode.

Wogoman, EP 0 206 218, published Dec. 30, 1986 discloses a biosensor having two electrodes, the electrodes being made of different electrically conducting materials. For example, the anode is formed from an anode material, such as platinum, and the cathode is formed from a cathode material, such as silver. The anode is coated with an enzyme. In a preferred embodiment, the coated electrode is covered with an elastomer that is permeable to glucose.

Pottgen et al., WO 89/08713, published Sep. 21, 1989, discloses the use of a two electrode biosensor, wherein the electrodes are made of the same noble metal, but one of the electrodes (referred to as a pseudoreference electrode) is larger than the other (working) electrode.

Conventional wisdom in the electrochemical arts suggests biosensors of the following types:

1) a three electrode system, wherein a working electrode is referenced against a reference electrode (such as silver/silver chloride) and a counter electrode provides a means for current flow;

2) a two electrode system, wherein the working and counter electrodes are made of different electrically conducting materials; and 3) a two electrode system, wherein the working and counter electrodes are made of the same electrically conducting materials, but the counter electrode is larger than the working electrode.

Conventional wisdom in the electrochemical arts does not suggest that a biosensor could include a two electrode system, wherein the working and counter electrodes are substantially the same size (or wherein the counter electrode is smaller than the working electrode) and made of the same electrically conducting material.

SUMMARY OF THE INVENTION

The invention is a new biosensor (an electrochemical device) and method of its use. The biosensor includes working and counter electrodes of substantially the same size, made of the same electrically conducting material, and affixed to a first electrical insulator. Overlaying the electrodes is a second electrical insulator that includes a cutout portion that exposes substantially equal surface areas of the working and counter electrodes.

A reagent is added to the cutout portion. The reagent substantially covers the exposed electrode surfaces in the cutout portion and includes a redox mediator, an enzyme and a buffer.

When a sample containing an analyte is added to the reagent, the analyte, enzyme, and the redox mediator participate in a reaction, wherein the redox mediator is either reduced (receives at least one electron) or is oxidized (donates at least one electron). Usually, in this reaction, the analyte is oxidized and the redox mediator is reduced. After this reaction (wherein analyte is oxidized and redox mediator is reduced) is complete, an electrical potential difference is applied between the electrodes. The amount of oxidized form of the redox mediator at the counter electrode and the applied potential difference must be sufficient to cause diffusion limited electrooxidation of the reduced form of the redox mediator at the surface of the working electrode. After a short time delay, current produced by the electrooxidation of the reduced form of the redox mediator is measured and the observed current is correlated to the amount of the analyte in the sample.

Importantly, only two electrodes of substantially the same size and made of the same electrically conducting material are required when the reagent includes a sufficient amount of the oxidized form of the redox mediator to insure that the current produced during electrooxidation is limited by the oxidation of the reduced form of the redox mediator at the working electrode surface.

For current produced during electrooxidation to be limited by the oxidation of the reduced form of the redox mediator at the working electrode surface, the amount of oxidized form of the redox mediator at the surface of the counter electrode must always exceed the amount of reduced form of the redox mediator at the surface to the working electrode.

DETAILED DESCRIPTION OF THE INVENTION

Figure 1:
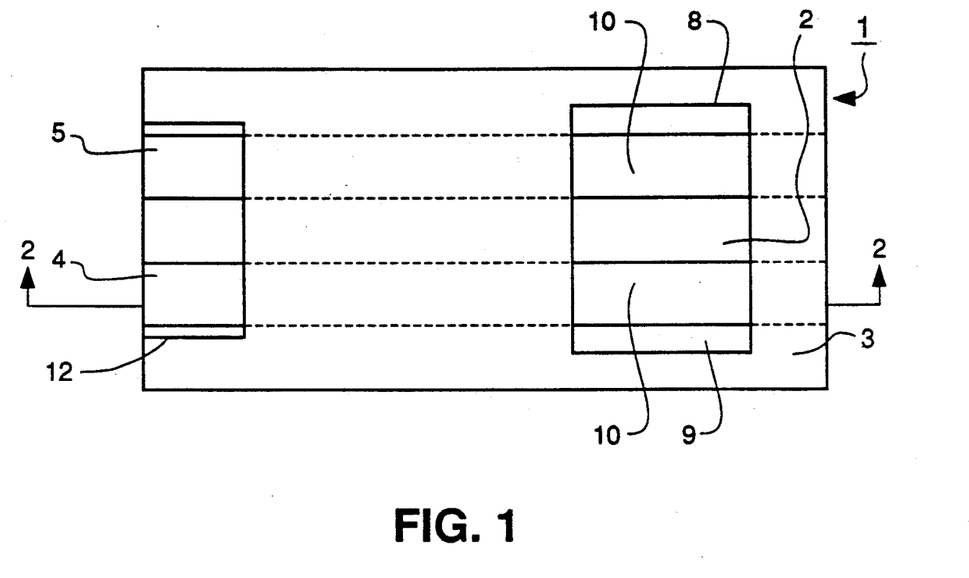
FIG. 1 is a schematic top view of a preferred embodiment of the inventive biosensor, excluding reagent and mesh covering.
Figure 2:
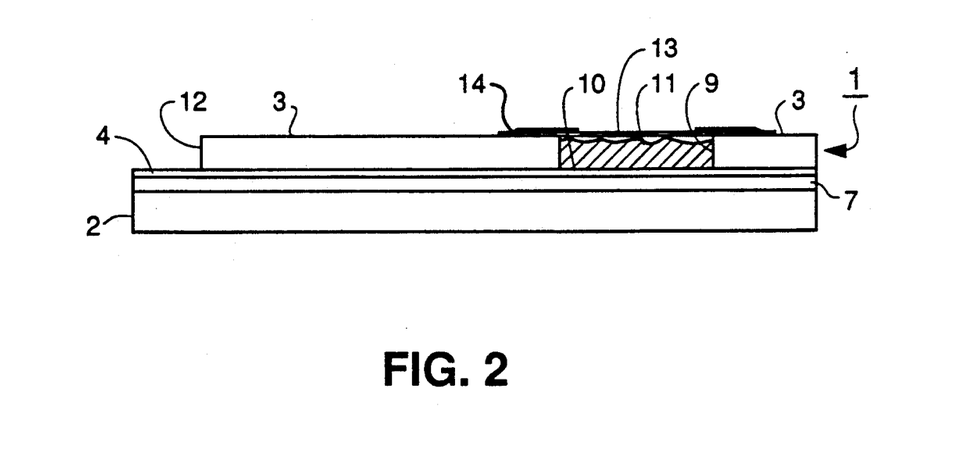
FIG. 2 is a schematic elevation of the inventive biosensor of FIG. 1 along lines 2—2, and including reagent and mesh covering.
Figure 3:
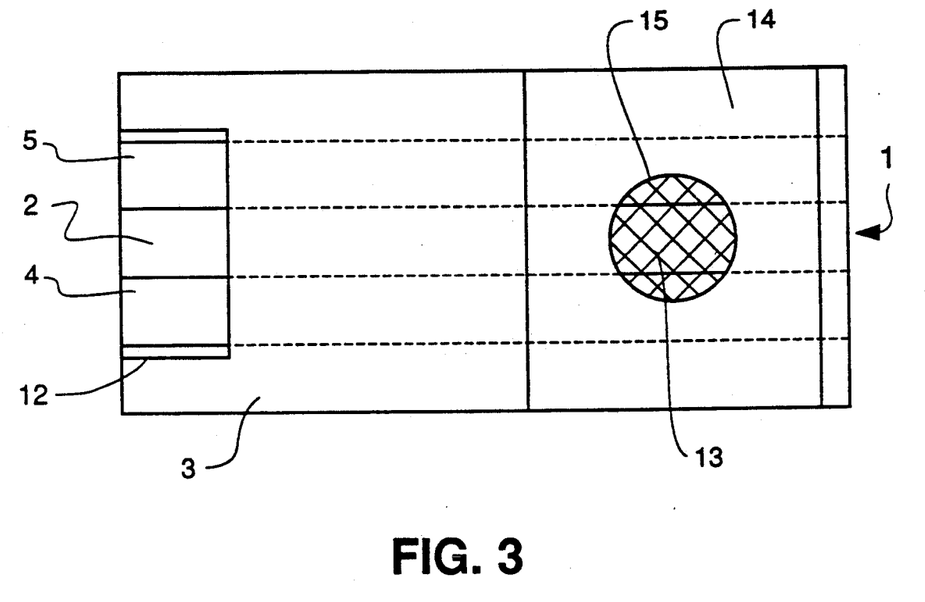
FIG. 3 is a schematic top view of a preferred embodiment of the inventive biosensor, including mesh covering.

Referring more specifically to FIGS. 1 through 3, there is shown the presently preferred embodiment of the biosensor of the present invention.

Biosensor 1 comprises first and second electrically insulating layers 2 and 3, respectively. Any useful insulating material will be suitable. Typically, plastics, such as vinyl polymers and polyimides provide the electrical and structural properties which are desired.

The biosensor shown in FIGS. 1 through 3 is intended to be mass produced from rolls of material, necessitating the selection of a material which is sufficiently flexible for roll processing and at the same time sufficiently stiff to give a useful stiffness to the finished biosensor.

Layers 2 and 3 may be of any useful thickness. In a preferred embodiment, layer 2 is about 360 microns thick and layer 3 is about 250 microns thick.

Working electrode 4 and counter electrode 5 are preferably deposited on a backing of insulator material 7, such as polyimide, to reduce the possibility of tearing the electrode before it is affixed to layer 2. Working electrode 4 and counter electrode 5 are substantially the same size and are made of the same electrically conducting material. Examples of electrically conducting materials that may be used are palladium, platinum, gold, silver, carbon, titanium, and copper. Noble metals are preferred because they provide a more constant, reproducible electrode surface area. Palladium is particularly preferred because it is one of the more difficult noble metals to oxidize and because it is a relatively inexpensive noble metal. Silver is not preferred because it is more readily oxidized by air than the other noble metals listed above. Preferably, electrodes 4 and 5 are about 0.1 micron thick and backing 7 is about 25 microns thick (commercially available from Courtalls Andus Performance Films in California and Southwall Technologies, Inc.) (FIG. 2).

Electrodes 4 and 5 must be sufficiently separated so that the electrochemical events at one electrode do not interfere with the electrochemical events at the other electrode. The preferred distance between electrodes 4 and 5 is about 1.2 millimeters (mm).

In the preferred embodiment, electrodes 4 and 5, affixed to backing 7, are unspooled from reels and attached to layer 2 by the use of hot melt adhesive (not shown). Electrodes 4 and 5 also preferably extend from one end of layer 2 to the other end in parallel configuration. (FIG. 1).

Insulating layer 3 is fixed on top of layer 2 and electrodes 4 and 5 by the use of hot melt adhesive (not shown). Layer 3 includes cut out portion 8, which defines reagent well 9 and exposes substantially equal surface areas 10 of electrodes 4 and 5.

In the preferred embodiment, cutout 8 is 4 mm by 6 mm and electrodes 4 and 5 are each 1.5 mm in width. Therefore, a surface area of about 6 mm² is exposed for each of the two electrodes.

Biosensor 1 also includes a power source (not shown) in electrical connection with the working and counter electrodes and a current measuring meter (not shown) which is also in electrical connection with the working and counter electrodes.

Biosensor reagent 11 (FIG. 2) is placed in well 9 so that it covers substantially all of exposed surfaces 10 of electrodes 4 and 5 and preferably covers the exposed surface of layer 2 between the electrodes.

At a minimum, reagent 11 includes the oxidized form of a redox mediator, an enzyme, and a buffer. The oxidized form of the redox mediator must be of sufficient type to receive at least one electron from a reaction involving enzyme, analyte, and oxidized form of the redox mediator. (The term redox mediator means a mediator that is capable of undergoing an electrochemical, reversible oxidation-reduction reaction.) The enzyme must be of sufficient type and in sufficient amount to catalyze the reaction involving enzyme, analyte and oxidized form of the redox mediator. The buffer must be of sufficient type and in sufficient amount to provide and maintain a pH where the enzyme catalyzes the reaction involving enzyme, analyte and oxidized form of the redox mediator.

Generally, when a sample containing the analyte is added to the reagent, the analyte is oxidized and the oxidized form of the redox mediator is reduced as shown below:

analyte + redox mediator
(oxidized form) (reduced form)

The reaction shown above is permitted to go to completion. (Completion is defined as sufficient reaction involving analyte, enzyme, and redox mediator (oxidized form) to correlate analyte concentration to diffusion limited current generated by oxidation of the reduced form of the redox mediator at the surface of the working electrode.) After reaction is complete, a power source (e.g., a battery) applies a potential difference between the electrodes. When the potential difference is applied, the amount of oxidized form of the redox mediator at the counter electrode and the potential difference must be sufficient to cause diffusion limited electrooxidation of the reduced form of the redox mediator at the working electrode surface. The diffusion limited current generated by the oxidation of the reduced form of the redox mediator at the working electrode surface is measured by a current measuring meter.

The measured current may be accurately correlated to the concentration of analyte in the sample when the following requirements are satisfied:

1) the rate of oxidation of the reduced form of the redox mediator is governed by the rate of diffusion of the reduced form of the redox mediator to the surface of the working electrode; and 2) the current produced is limited by the oxidation of the reduced form of the redox mediator at the surface of the working electrode.

In the present inventive device, these requirements are satisfied by employing a readily reversible redox mediator and by supplying reagent 11 with the oxidized form of the redox mediator in an amount sufficient to insure that the current produced during diffusion limited electrooxidation is limited by the oxidation of the reduced form of the redox mediator at the working electrode surface. For current produced during electrooxidation to be limited by the oxidation of the reduced form of the redox mediator at the working electrode surface, the amount of oxidized form of the redox mediator at the surface of the counter electrode must always exceed the amount of the reduced form of the redox mediator at the surface of the working electrode.

Importantly, when the reagent includes an excess of the oxidized form of the redox mediator, as described below, the working and counter electrodes may be substantially the same size as well as made of the same electrically conducting material. The ability to utilize electrodes that are substantially the same size and made of the same material represents an important advantage for manufacturing a biosensor.

A further requirement of the reagent is that the buffer employed must have a higher oxidation potential than the reduced form of the redox mediator.

The type of enzyme used will depend upon the analyte to be measured. For example, if glucose is the analyte to be measured, glucose oxidase may be used as the enzyme. If cholesterol is the analyte to be measured, cholesterol oxidase may be used as the enzyme.

As explained above, the redox mediator must be readily reversible and the oxidized form of the redox mediator must be of sufficient type to receive at least one electron from the reaction involving enzyme, analyte, and oxidized form of the redox mediator. For example, when glucose is the analyte to be measured and glucose oxidase is the enzyme, ferricyanide or quinone may be the oxidized form of the redox mediator.

Other examples of enzymes and redox mediators (oxidized form) that may be used in measuring particular analytes by the present invention are listed below in Table 1.

The amount of enzyme included in the reagent may vary depending upon the time period desired for completion of the reaction involving analyte, enzyme, and oxidized form of the redox mediator. The more enzyme added, the shorter the time period for completion of the reaction. When a glucose reagent includes glucose oxidase, more than about 0.5 million units of glucose oxidase per liter of reagent (referring to the reagent composition before being dried on the electrode surfaces) should be used in the reagent, and preferably about 2 million units of glucose oxidase per liter of reagent is used. Below about 0.5 million units per liter of reagent, assay performance is poor. About 2 million units of glucose oxidase per liter of reagent provides a reagent that will achieve completion of the reaction involving glucose, glucose oxidase, and ferricyanide within about 20 seconds, a conveniently short time period for the reaction. Above about 2 million units of glucose oxidase per liter of reagent, the reagent is needlessly more expensive to produce. (These amounts of glucose oxidase refer to the reagent composition before it is dried onto the electrode surfaces.)

The actual amount of oxidized form of the redox mediator needed in the reagent is governed by the concentration range of the analyte sought to be measured. The reagent for analyzing glucose (described herein) includes sufficient redox mediator (oxidized form) to measure the glucose level in a sample of human whole blood from about 10 to about 70 microliters ($\mu l$) in volume. The reagent must be provided with enough of

TABLE I

| ANALYTE | ENZYMES | REDOX MEDIATOR (OXIDIZED FORM) | ADDITIONAL MEDIATOR |
|---|---|---|---|
| GLUCOSE | GLUCOSE DEHYDROGENASE AND DIAPHORASE | FERRICYANIDE | |
| CHOLESTEROL | CHOLESTEROL ESTERASE AND CHOLESTEROL OXIDASE | FERRICYANIDE | 2,6-DIMETHYL-1,4-BENZOQUINONE 2,5-DICHLORO-1,4-BENZOQUINONE OR PHENAZINE ETHOSULFATE |
| HDL CHOLESTEROL | CHOLESTEROL ESTERASE AND CHOLESTEROL OXIDASE | FERRICYANIDE | 2,6-DIMETHYL-1,4-BENZOQUINONE 2,5-DICHLORO-1,4-BENZOQUINONE OR PHENAZINE ETHOSULFATE |
| TRIGLYCERIDES | LIPOPROTEIN LIPASE, GLYCEROL KINASE, AND GLYCEROL-3-PHOSPHATE OXIDASE | FERRICYANIDE OR PHENAZINE ETHOSULFATE | PHENAZINE METHOSULFATE |
| LACTATE | LACTATE OXIDASE | FERRICYANIDE | 2,6-DICHLORO-1,4-BENZOQUINONE |
| LACTATE | LACTATE DEHYDROGENASE AND DIAPHORASE | FERRICYANIDE, PHENAZINE ETHOSULFATE, OR PHENAZINE METHOSULFATE | |
| LACTATE DEHYDROGENASE | DIAPHORASE | FERRICYANIDE, PHENAZINE ETHOSULFATE, OR PHENAZINE METHOSULFATE | |
| PYRUVATE | PYRUVATE OXIDASE | FERRICYANIDE | |
| ALCOHOL | ALCOHOL OXIDASE | PHENYLENEDIAMINE | |
| BILIRUBIN | BILIRUBIN OXIDASE | 1-METHOXY-PHENAZINE METHOSULFATE | |
| URIC ACID | URICASE | FERRICYANIDE | |

In some of the examples shown in Table 1, at least one additional enzyme is used as a reaction catalyst. Also, some of the examples shown in Table 1 may utilize an additional mediator, which facilitates electron transfer to the oxidized form of the redox mediator. The additional mediator may be provided to the reagent in lesser amount than the oxidized form of the redox mediator.

the oxidized form of the redox mediator so that when the potential difference is applied between electrodes 4 and 5, the amount of oxidized form of the redox mediator at the surface of the counter electrode exceeds the amount of reduced form of the redox mediator at the working electrode.

The upper limit of the amount of redox mediator (oxidized form) will usually depend on the mediator's solubility and dispersion properties in the reagent. The reagent for the present invention, exemplified by a biosensor for the assay of glucose, preferably includes a microcrystalline material of sufficient type and in sufficient amount to disperse the redox mediator in the reagent.

Examples of microcrystalline materials that will disperse the redox mediator are microcrystalline cellulose, dextrans, and chitin. The amount of microcrystalline material included in the preferred glucose reagent, which includes glucose oxidase and potassium ferricyanide, is from about 1% (weight:volume) to about 4.5% (weight:volume), and is preferably about 1.5% (weight:volume). Below about 1% (weight:volume) microcrystalline material, the reagent will fall off of the electrode surfaces after drying. Above about 4.5% (weight:volume) microcrystalline material, the reagent gels. For a glucose reagent that includes ferricyanide and glucose oxidase, the preferred microcrystalline material is a combination of AVICEL RC-591F (a microcrystalline cellulose available from FMC Corp.) and NATROSOL-250 M (a micro-crystalline hydroxyethylcellulose available from Aqualon). The amount of AVICEL in the reagent may range to from about 1% to about 4.2% (weight:volume) and is preferably about 1.4% (weight:volume). The amount of NATROSOL in the reagent may range from about 0% to about 0.3% (weight:volume) and is preferably about 0.06% (weight:volume). (These percentages refer to the reagent composition before it is dried onto the electrode surfaces.)

When AVICEL and NATROSOL are added to the reagent, in the ranges stated above, the amount of potassium ferricyanide that may be incorporated into the reagent may range from about 0.15 molar (M) to about 0.7M, and is preferably about 0.3M. When the concentration of ferricyanide is below about 0.15M and above about 0.7M, performance of the biosensor decreases. (These molarities refer to the reagent composition before it is dried onto the electrode surfaces.)

The reagent also preferably includes a surfactant of sufficient type and in sufficient amount to wet a sample containing the analyte to be measured. For example, in a reagent for analyzing a sample of human whole blood containing glucose, the surfactant is preferably a non-ionic surfactant. From about 0% (weight:volume) to about 0.3% (weight:volume) surfactant may be present in the reagent. Above about 0.3% (weight:volume) surfactant, red blood cells begin to hemolyze. The preferred surfactant in the glucose reagent is TRITON X-100 (available from Sigma Chemical Corporation) at a preferred concentration of about 0.05% (weight:volume.). (Percentages refer to the reagent composition before it is dried onto the electrode surfaces.)

Any buffer that satisfies the above-stated requirements of providing a satisfactory pH for enzyme function and having a higher oxidation potential than the reduced form of the redox mediator may be used.

Examples of such buffers for a glucose reagent utilizing the enzyme glucose oxidase include phosphate, citrate (citrate also helps stabilize the reagent), "Good" buffers (e.g., 2-(N-morpholino) ethanesulfonic acid, N-(2-acetamido)-2-iminodiacetic acid, piperazine-N,N'-bis (2-ethanesulfonic acid), N-(2- acetamido)-2-aminoethanesulfonic acid, N,N-bis (2-hydroxyethyl)-2-aminoethanesulfonic acid, N- tris (hydroxymethyl)methyl-methyl-2-aminoethanesulfonic acid, and N-2-(hydroxymethyl)methylpiperazine - N'- 2- ethanesulfonic acid, and Tris buffers (buffers derived from 2-amino- 2 (hydroxymethyl) -1,3-propanediol). ("Good" and Tris buffers are available from Sigma Chemical Company.) Imidazole should not be used as a buffer. These buffers may be used to provide a preferred pH range from about 4 to about 8. The most preferred pH range is from about 6 to about 7. The most preferred buffer is phosphate (e.g., potassium phosphate) from about 0.1M to about 0.5M and preferably about 0.4M. (These concentration ranges refer to the reagent composition before it is dried onto the electrode surfaces.)

The reagent preferably further includes a reagent stabilizer of sufficient type and in sufficient amount to stabilize the reagent. The reagent stabilizer stabilizes the enzyme, and for a glucose reagent containing glucose oxidase, the reagent stabilizer may be selected from a group consisting of glutamate, aspartate, blue dextran and trehalose. The preferred reagent stabilizer for a reagent containing glucose oxidase is glutamate (e.g., potassium glutamate) at a concentration range from about 0% (weight:volume) to about 4% (weight:volume), with the preferred amount being about 2% (weight:volume). (These percentages refer to the reagent composition before it is dried onto the electrode surfaces.)

A protocol for making the preferred glucose reagent utilizing the enzyme glucose oxidase and ferricyanide as the oxidized form of the redox mediator is as follows:

Step 1—Prepare 1 liter (in a volumetric flask) of a buffer/NATROSOL mixture by adding 1.2000 grams (g) NATROSOL-250M to 0.740M aqueous potassium phosphate buffer (including 80.062 g monobasic potassium phosphate and 26.423 g dibasic potassium phosphate) at pH 6.25. Allow the NATROSOL to stir and swell for 3 hours.

Step 2—Prepare an AVICEL mixture by stirring 14.0000 g AVICEL RC-591 F and 504.7750 g water for 20 minutes.

Step 3—Prepare a TRITON mixture by adding 0.5000 g TRITON X-100 to 514.6000 g of the buffer/NATROSOL mixture and stir for 15 minutes.

Step 4—While stirring, add the total TRITON mixture dropwise with a dropwise addition funnel or buret to the total AVICEL mixture. Once addition is complete, continue stirring overnight.

Step 5—To the mixture resulting from Step 4, add, while stirring, 98.7750 g potassium ferricyanide. (Add a little potassium ferricyanide at a time to allow the potassium ferricyanide to dissolve as added.)

Step 6—Stir the resulting mixture of Step 5 for 20 minutes.

Step 7—Adjust the pH of the mixture resulting from Step 6 to 6.25 by adding potassium hydroxide.

Step 8—To the resulting mixture of Step 7 add 9.1533 g glucose oxidase (218.50 units per milligram (mg) from Biozyme) and stir at least 20 minutes.

Step 9—To the resulting mixture of Step 8 add 20 g potassium glutamate and stir at least 20 minutes.

Step 10—Filter the resulting mixture of Step 9 through a 100 micron sieve bag to remove any AVICEL clumping. The filtrate is the resulting reagent composition, which is added to the electrode surfaces and is then dried.

In the preferred embodiment for glucose determination, 6 microliters ($\mu$l) of reagent made by the above-stated protocol is added to well 9 formed by cutout 8. This amount of reagent 11 will substantially cover surface areas 10 on both electrodes (FIGS. 1 and 2) and will also contain a sufficient amount of ferricyanide, and a sufficient amount of enzyme (glucose oxidase) to catalyze the oxidation of glucose (from a sample of human whole blood) and the reduction of ferricyanide to completion within about 20 seconds.

Reagent 11 is then dried by heating at about 50° C. for about 3 minutes. Drying removes at least about 90% of the water content of the reagent, thereby resulting in a preferred dried reagent with the following proportions of components: from about 0.8 to about 1.0 millimole (mmol) ferricyanide per gram of dried reagent; from about 2,300 to about 2,600 units of glucose oxidase per gram of dried reagent, assuming 75% loss of enzyme activity (an unusually high loss of enzyme activity) from reagent drying, from about 8,600 to about 9,600 units of glucose oxidase per gram of dried reagent, assuming a more typical 6% loss of enzyme activity from reagent drying, and from about 9,200 to about 10,400 units of glucose oxidase per gram of dried reagent, assuming no loss of enzyme activity from reagent drying; from about 1.3 to about 1.9 m mol phosphate buffer per gram of dried reagent; from about 2 to about 3 milligrams (mg) NATROSOL-250M per gram of dried reagent and from about 50 to about 71 mg AVICEL RC-591 F per gram of dried reagent (a total of from about 52 to about 74 mg microcrystalline material per gram of dried reagent); from about 71 to about 102 mg glutamate per gram of dried reagent; and from about 2 to about 3 mg TRITON X-100 per gram of dried reagent.

As stated above, each component of the formulated reagent (before drying) may vary within the disclosed limits. Accordingly, numerical ranges of amounts of each component in a dried reagent (wherein at least about 90% of the water content of the reagent has been removed) will be broader than the ranges stated above for the preferred formulation.

After drying, a polyester or nylon mesh 13 (FIGS. 2 and 3) is preferably placed on top of the dried reagent to aid in preventing loss of reagent from the biosensor during shipping and handling and to aid in minimizing human contamination from the reagent. Mesh 13 is affixed to the inventive device by adhesive tape 14, which includes hole 15. (FIGS. 2 and 3) Hole 15 is the target area for adding a sample containing an analyte to be measured by the inventive device. (FIG. 3)

After drying the reagent and affixing the mesh, the roll-formed biosensors are separated by die punching to form discrete biosensors, which are used in conjunction with 1) a power source in electrical connection with the working and counter electrodes and capable of supplying an electrical potential difference between the working and counter electrodes sufficient to cause diffusion limited electrooxidation of the reduced form of the redox mediator at the surface of the working electrode, and 2) a meter in electrical connection with the working and counter electrodes and capable of measuring the diffusion limited current produced by oxidation of the reduced form of the redox mediator when the above-stated electrical potential difference is applied.

The meter described above will normally be adapted to apply an algorithm to the current measurement, whereby an analyte concentration is provided and visually displayed. Improvements in such a power source and meter are the subject of commonly assigned U.S. Pat. No. 4,963,814 (issued Oct. 16, 1990), and U.S. Pat. No. 4,999,632, issued Mar. 12, 1991 (application Ser. No. 07/451,212, filed Dec. 15, 1989), U.S. Pat. No. 4,999,582, issued Mar. 12, 1991 (application Ser. No. 07/451,108, filed Dec. 15, 1989), and U.S. patent application Ser. No. 07/451,309, filed Dec. 15, 1989, now U.S. Pat. No. 5,243,516, the disclosures of which are hereby incorporated by reference.

For easy electrical connection of the power source and meter, additional cutout portion 12 (FIGS. 1 through 3), exposing portions of the working and counter electrodes, are preferably provided in the biosensor device.

The biosensor device described above may be used to determine the concentration of an analyte in a fluid sample by performing the following steps:

a) contacting the fluid sample with a reagent (described above) that substantially covers substantially equal surface areas of working and counter electrodes;

b) allowing the reaction between the analyte and the oxidized form of the redox mediator to go to completion;

c) subsequently applying a potential difference between the electrodes sufficient to cause diffusion limited electrooxidation of the reduced form of the redox mediator at the surface of the working electrode;

d) thereafter measuring the resulting diffusion limited current; and e) correlating the current measurement to the concentration of analyte in the fluid.

Many analyte-containing fluids may be analyzed. For example, analytes in human body fluids such as whole blood, blood serum, urine and cerebrospinal fluid may be measured. Also, analytes found in fermentation products and in environmental substances, which potentially contain environmental contaminants, may be measured.

When measuring analytes found in human body fluids, especially whole blood, the potential difference applied between the electrodes should be no more than about 500 millivolts. When a potential difference above about 500 millivolts is applied between the electrodes, oxidation of the working electrode surface (for palladium) and of some blood components can become intolerable, thereby preventing an accurate and precise correlation of current to analyte concentration. For an assay of glucose in a whole blood sample, wherein the oxidized form of the redox mediator is ferricyanide, a potential difference from about 150 millivolts to about 500 millivolts may be applied between the electrodes to achieve diffusion limited electrooxidation of the reduced form of the redox mediator at the surface of the working electrode. Preferably, about 300 millivolts potential difference is applied between the electrodes.

Current generated from the oxidation of the reduced form of the redox mediator may be measured at any time from about 0.5 seconds to about 30 seconds after the potential difference is applied between the electrodes. At less than about 0.5 seconds, diffusion limited current has not been achieved. After about 30 seconds, convection becomes significant, thereby interfering with the measurement of a diffusion limited current. Preferably, current is measured at about 10 seconds after the potential difference is applied between the electrodes, and the measured current is correlated to the concentration of analyte in the sample.

In the preferred method for analysis of glucose from a sample of human whole blood, 20 $\mu$l of whole blood is added to the above-stated preferred glucose reagent. The reaction of glucose and ferricyanide is allowed to go to completion, thereby forming gluconic acid and ferrocyanide. This reaction normally requires a short time to go to completion, and in the preferred embodiment, the reaction goes to completion in less than about 20 seconds. About twenty seconds after addition of the whole blood sample, a potential difference of about 300 millivolts is applied between the electrodes, thereby oxidizing ferrocyanide to ferricyanide at the surface of the working electrode. About 10 seconds after the potential difference is applied to the electrodes, current is measured and correlated to the concentration of glucose in the blood sample.

The glucose concentration of a sample may be accurately and precisely measured by the present inventive method utilizing the present inventive biosensor. Further, when a sample of human whole blood is measured, error due to hematocrit effect is insignificant.

As a variation of the present invention, the counter electrode could be smaller than the working electrode. When the counter electrode is smaller than the working electrode, the amount of oxidized form of the redox mediator supplied to reagent 11 must be increased. The amount of oxidized form of the redox mediator in reagent 11 must be increased because the above-stated requirements for accurately correlating concentration of the analyte to current must be satisfied; that is, 1) the rate of oxidation of the reduced form of the redox mediator is governed by the rate of diffusion of the reduced form of the redox mediator to the surface of the working electrode; and 2) the current produced is limited by the oxidation of the reduced form of the redox mediator at the surface of the working electrode.

For example, it has been shown that when the counter electrode is about half the size of the working electrode, a mixture of about 2700 nanomoles (nmol) of ferricyanide and about 900 nmol of ferrocyanide (dissolved in 20 μl of water) satisfied the requirements stated above.

Also, the present invention has been illustrated by analytes that are oxidized and redox mediators that are reduced in the presence of a catalytic amount of enzyme. However, the present inventive device, reagents and methods may also be used to measure the concentration of an analyte in a fluid sample, wherein the analyte is reduced and the reduced form of a redox mediator is oxidized in the presence of a catalytic amount of an enzyme (e.g., a reductase). After the reaction involving analyte, enzyme, and reduced form of the redox mediator reaches completion, a potential difference is applied between the electrodes. The amount of reduced form of the redox mediator at the counter electrode (in this case an anode rather than a cathode) and the applied potential difference must be sufficient to cause diffusion limited electroreduction of the oxidized form of the redox mediator at the surface of the working electrode (in this case a cathode rather than an anode). The diffusion limited current generated by reduction of the oxidized form of the the redox mediator at the working electrode surface is correlated to the concentration of analyte in the sample being analyzed.

The redox mediator must be readily reversible and the amount of reduced form of the redox mediator in reagent 11 must be sufficient to insure that the current produced during electroreduction is limited by the reduction of the oxidized form of the redox mediator at the working electrode surface.

The buffer must also have a lower reduction potential than the reduction potential of the oxidized form of the redox mediator and must be of sufficient type and in sufficient amount to provide and maintain a pH at which the enzyme catalyzes the reaction involving analyte, enzyme and the reduced form of the redox mediator. These and other requirements are analogous to those for measuring an analyte that is oxidized rather than reduced.

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

What is claimed is:

1. A device for analyzing an analyte, comprising:
   a. a first electrical insulator;
   b. a pair of electrodes consisting of working and counter electrodes of substantially the same size, the electrodes being made of the same electrically conducting materials and being supported on the first electrical insulator;
   c. a second electrical insulator, overlaying the first electrical insulator and the electrodes and including a cutout portion that exposes substantially equal surface areas of the working and counter electrodes; and
   d. a reagent, substantially covering the exposed electrode surfaces in the cutout portion and comprising the oxidized form of a redox mediator, an enzyme, and a buffer,
   the oxidized form of the redox mediator being of sufficient type to receive at least one electron from a reaction involving enzyme, analyte, and oxidized form of the redox mediator and being in sufficient amount to insure that current produced by diffusion limited electrooxidation is limited by the oxidation of the reduced form of the redox mediator at the working electrode surface,
   the enzyme being of sufficient type and in sufficient amount to catalyze the reaction involving enzyme, analyte, and oxidized form of the redox mediator, and
   the buffer having a higher oxidation potential than the reduced form of the redox mediator and being of sufficient type and in sufficient amount to provide and maintain a pH at which the enzyme catalyzes the reaction involving enzyme, analyte, and oxidized form of the redox mediator.

2. The device of claim 1, wherein the reagent further comprises a microcrystalline material of sufficient type and in sufficient amount to disperse the redox mediator in the reagent.

3. The device of claim 2, wherein the reagent further comprises a surfactant of sufficient type and in sufficient amount to wet a sample containing the analyte.

4. The device of claim 3, wherein the reagent further comprises a reagent stabilizer of sufficient type and in sufficient amount to stabilize the reagent.

5. The device of claim 4, wherein the analyte is glucose, the oxidized form of the redox mediator is ferricyanide, the buffer is phosphate, the microcrystalline material includes microcrystalline cellulose and microcrystalline hydroxyethylcellulose, the enzyme is glucose oxidase, the surfactant is a nonionic surfactant and the reagent stabilizer is selected from a group consisting of glutamate, aspartate, blue dextran, and trehalose.

6. The device of claim 2, wherein the analyte is glucose, the oxidized form of the redox mediator is ferricyanide and the enzyme is glucose oxidase.

7. The device of claim 1, wherein the reagent further comprises at least one additional enzyme and an additional redox mediator.

8. The device of claim 1, wherein the electrically conducting material of the working and counter electrodes is selected from a group consisting of palladium, platinum, gold, silver, titanium, copper, and carbon.

9. The device of claim 1, wherein the analyte is glucose, the oxidized form of the redox mediator is ferricyanide, and the enzyme is glucose oxidase.

10. The device of claim 9, further comprising:
   e. a power source in electrical connection with the working and counter electrodes and capable of supplying an electrical potential difference between the working and counter electrodes sufficient to cause diffusion limited electrooxidation of the reduced form of the redox mediator at the surface of the working electrode; and
   f. a meter in electrical connection with the working and counter electrodes and capable of measuring the diffusion limited current produced by the oxidation of the reduced form of the redox mediator at the working electrode surface.

11. The device of claim 1, further comprising:
   e. a power source in electrical connection with the working and counter electrodes and capable of supplying an electrical potential difference between the working and counter electrodes sufficient to cause diffusion limited electrooxidation of the reduced form of the redox mediator at the surface of the working electrode; and
   f. a meter in electrical connection with the working and counter electrodes and capable of measuring the diffusion limited current produced by the oxidation of the reduced form of the redox mediator at the working electrode surface.

12. A device for analyzing glucose, comprising:
   a. a first electrical insulator;
   b. a pair of electrodes consisting of working and counter electrodes of substantially the same size, the electrodes being made of palladium and being supported on the first electrical insulator;
   c. a second electrical insulator overlaying the first electrical insulator and the electrodes and including a cutout portion that exposes substantially equal surface areas of the working and counter electrodes; and
   d. a reagent, substantially covering the exposed electrode surfaces in the cutout portion and comprising
   1) from about 1.1 to about 1.5 millimoles ferricyanide per gram of reagent,
   2) from about 1.3 to about 1.9 millimoles phosphate buffer per gram of reagent,
   3) from about 2,300 to about 10,400 units of glucose oxidase per gram of reagent,
   4) from about 50 to about 71 milligrams microcrystalline cellulose per gram of reagent,
   5) from about 2 to about 3 milligrams microcrystalline hydroxyethylcellulose per gram of reagent,
   6) from about 2 to about 3 milligrams TRITON X-100 per gram of reagent, and
   7) from about 71 to about 102 milligrams glutamate per gram of reagent.

13. The device of claim 12, wherein the second electrical insulator further includes an additional cutout portion exposing portions of the working and counter electrodes, and the device further comprises:
   e. a power source in electrical connection with the working and counter electrodes at the additional cutout portion, the power source being capable of supplying an electrical potential difference between the working and counter electrodes sufficient to cause diffusion limited electrooxidation of the reduced form of the ferricyanide at the surface of the working electrode; and
   f. a meter in electrical connection with the working and counter electrodes and capable of measuring the diffusion limited current produced by the oxidation of the reduced form of the ferricyanide at the working electrode surface.

14. A reagent incorporated into a sample receiving portion of an electrochemical device that measures an analyte and that has a pair of electrodes consisting of working and counter electrodes of substantially the same size, the electrodes being made of the same electrically conducting materials and having substantially equal surface areas in the sample receiving portion, comprising:
   the oxidized form of a redox mediator, an enzyme, and a buffer,
   the oxidized form of the redox mediator being of sufficient type to receive at least one electron from a reaction involving enzyme, analyte, and oxidized form of the redox mediator and being in sufficient amount to insure that current produced by diffusion limited electrooxidation is limited by the oxidation of the reduced form of the redox mediator at the working electrode surface,
   the enzyme being of sufficient type and in sufficient amount to catalyze the reaction involving enzyme, analyte, and oxidized form of the redox mediator, and
   the buffer having a higher oxidation potential than the reduced form of the redox mediator and being of sufficient type and in sufficient amount to provide and maintain a pH at which the enzyme catalyzes the reaction involving enzyme, analyte, and oxidized form of the redox mediator.

15. The reagent of claim 14, wherein the reagent further comprises at least one additional enzyme and an additional redox mediator.

16. The reagent of claim 14, further comprising:
   a microcrystalline material of sufficient type and in sufficient amount to disperse the redox mediator in the reagent.

17. The reagent of claim 16, further comprising:
   a surfactant of sufficient type and in sufficient amount to wet a sample containing the analyte.

18. The reagent of claim 17, further comprising:
   a reagent stabilizer of sufficient type and in sufficient amount to stabilize the reagent.

19. The device of claim 18, wherein the analyte is glucose, the oxidized form of the redox mediator is ferricyanide, the buffer is phosphate, the microcrystalline material includes microcrystalline cellulose and microcrystalline hydroxyethylcellulose, the enzyme is glucose oxidase, the surfactant is a nonionic surfactant and the reagent stabilizer is selected from a group consisting of glutamate, aspartate, blue dextran, and trehalose.

20. A reagent incorporated into a sample receiving portion of an electrochemical device that measures glucose and that has a pair of electrodes consisting of working and counter electrodes of substantially the same size, the electrodes being made of the same electrically conducting materials and having substantially equal surface areas in the sample receiving portion, comprising:
  a. from about 1.1 to about 1.5 millimoles ferricyanide per gram of reagent;
  b. from about 1.3 to about 1.9 millimoles phosphate buffer per gram of reagent;
  c. from about 2,300 to about 10,400 units of glucose oxidase per gram of reagent;
  d. from about 50 to about 71 milligrams microcrystalline cellulose per gram of reagent;
  e. from about 2 to about 3 milligrams microcrystalline hydroxyethylcellulose per gram of reagent;
  f. from about 2 to about 3 milligrams TRITON X-100 per gram of reagent; and
  g. from about 71 to about 102 milligrams glutamate per gram of reagent.

21. A device for analyzing an analyte, comprising:
  a. a first electrical insulator;
  b. a pair of electrodes consisting of working and counter electrodes of substantially the same size, the electrodes being made of the same electrically conducting materials and being supported on the first electrical insulator;
  c. a second electrical insulator, overlaying the first electrical insulator and the electrodes and including a cutout portion that exposes substantially equal surface areas of the working and counter electrodes; and
  d. a reagent, substantially covering the exposed electrode surfaces in the cutout portion and comprising the reduced form of a redox mediator, an enzyme, and a buffer,
  the reduced form of the redox mediator being of sufficient type to donate at least one electron from a reaction involving enzyme, analyte, and reduced form of the redox mediator and being in sufficient amount to insure that current produced by diffusion limited electroreduction is limited by the reduction of the oxidized form of the redox mediator at the working electrode surface,
  the enzyme being of sufficient type and in sufficient amount to catalyze the reaction involving enzyme, analyte, and the reduced form of the redox mediator, and
  the buffer having a lower reduction potential than the oxidized form of the redox mediator and being of sufficient type and in sufficient amount to provide and maintain a pH at which the enzyme catalyzes the reaction involving enzyme, analyte, and the reduced form of the redox mediator.

22. The device of claim 21, wherein the reagent further comprises
  a microcrystalline material of sufficient type and in sufficient amount to disperse the redox mediator in the reagent;
  a surfactant of sufficient type and in sufficient amount to wet a sample containing the analyte; and
  a reagent stabilizer of sufficient type and in sufficient amount to stabilize the reagent.

23. The device of claim 21, further comprising:
  e. a power source in electrical connection with the working and counter electrodes and capable of supplying an electrical potential difference between the working and counter electrodes sufficient to cause diffusion limited electroreduction of the oxidized form of the redox mediator at the surface of the working electrode; and
  f. a meter in electrical connection with the working and counter electrodes and capable of measuring the diffusion limited current produced by the reduction of the oxidized form of the redox mediator at the working electrode surface.

24. A reagent incorporated into a sample receiving portion of an electrochemical device that measures an analyte and that has a pair of electrodes consisting of working and counter electrodes of substantially the same size, the electrodes being made of the same electrically conducting materials and having substantially equal surface areas in the sample receiving portion, comprising:
  the reduced form of a redox mediator, an enzyme, and buffer,
  the reduced form of the redox mediator being of sufficient type to donate at least one electron from a reaction involving enzyme, analyte, and reduced form of the redox mediator and being in sufficient amount to insure that current produced by diffusion limited electroreduction is limited by the reduction of the oxidized form of the redox mediator at the working electrode surface,
  the enzyme being of sufficient type and in sufficient amount to catalyze the reaction involving enzyme, analyte, and the reduced form of the redox mediator, and
  the buffer having a lower reduction potential than the oxidized form of the redox mediator and being of sufficient type and in sufficient amount to provide and maintain a pH at which the enzyme catalyzes the reaction involving enzyme, analyte, and the reduced form of the redox mediator.

25. The reagent of claim 24, further comprising:
  a microcrystalline material of sufficient type and in sufficient amount of disperse the redox mediator in the reagent;
  a surfactant of sufficient type and in sufficient amount to wet a sample containing the analyte; and
  a reagent stabilizer of sufficient type and in sufficient amount to stabilize the reagent.

26. A device for analyzing an analyte, comprising:
  a. a first electrical insulator;
  b. a pair of electrodes consisting of a working electrode and a counter electrode that is smaller than the working electrode, the electrodes being made of the same electrically conducting materials and being supported on the first electrical insulator;
  c. a second electrical insulator, overlaying the first electrical insulator and the electrodes and including a cutout portion that exposes a smaller surface area of the counter electrode than the working electrode; and
  d. a reagent, substantially covering the exposed electrode surfaces in the cutout portion and comprising the oxidized form of a redox mediator, an enzyme, and a buffer,
  the oxidized form of the redox mediator being of sufficient type to receive at least one electron from a reaction involving enzyme, analyte, and oxidized form of the redox mediator and being in sufficient amount to insure that current produced by diffusion limited electrooxidation is limited by the oxidation of the reduced form of the redox mediator at the working electrode surface, the enzyme being of sufficient type and in sufficient amount to catalyze the reaction involving enzyme, analyte, and oxidized form of the redox mediator, and the buffer having a higher oxidation potential than the reduced form of the redox mediator and being of sufficient type and in sufficient amount to provide and maintain a pH at which the enzyme catalyzes the reaction involving enzyme, analyte, and oxidized form of the redox mediator.

27. The device of claim 26, wherein the reagent further comprises a microcrystalline material of sufficient type and in sufficient amount to disperse the redox mediator in the reagent.

28. The device of claim 27, wherein the analyte is glucose, the oxidized form of the redox mediator is ferricyanide and the enzyme is glucose oxidase.

29. The device of claim 27, wherein the reagent further comprises a surfactant of sufficient type and in sufficient amount to wet a sample containing the analyte.

30. The reagent of claim 29, wherein the reagent further comprises a reagent stabilizer of sufficient type and in sufficient amount to stabilize the reagent.

31. The device of claim 30, wherein the analyte is glucose, the oxidized form of the redox mediator is ferricyanide, the buffer is phosphate, the microcrystalline material includes microcrystalline cellulose and microcrystalline hydroxyethylcellulose, the enzyme is glucose oxidase, the surfactant is a nonionic surfactant and the reagent stabilizer is selected from a group consisting of glutamate, aspartate, blue dextran, and trehalose.

32. The device of claim 26, wherein the reagent further comprises at least one additional enzyme and an additional redox mediator.

33. The device of claim 26, wherein the electrically conducting material of the working and counter electrodes is selected from a group consisting of palladium, platinum, gold, silver, titanium, copper, and carbon.

34. The device of claim 26, wherein the analyte is glucose, the oxidized form of the redox mediator is ferricyanide, and the enzyme is glucose oxidase.

35. The device of claim 26, further comprising:
e. a power source in electrical connection with the working and counter electrodes and capable of supplying an electrical potential difference between the working and counter electrodes sufficient to cause diffusion limited electrooxidation of the reduced form of the redox mediator at the surface of the working electrode; and
f. a meter in electrical connection with the working and counter electrodes and capable of measuring the diffusion limited current produced by the oxidation of the reduced form of the redox mediator at the working electrode surface.

36. A device for analyzing an analyte, comprising:
a. a first electrical insulator;
b. a pair of electrodes consisting of a working electrode and a counter electrode that is smaller than the working electrode, the electrodes being made of the same electrically conducting materials and being supported on the first electrical insulator;
c. a second electrical insulator, overlaying the first electrical insulator and the electrodes and including a cutout portion that exposes a smaller surface area of the counter electrode than the working electrode; and
d. a reagent, substantially covering the exposed electrode surfaces in the cutout portion and comprising the reduced form of a redox mediator, an enzyme, and a buffer, the reduced form of the redox mediator being of sufficient type to donate at least one electron from a reaction involving enzyme, analyte, and reduced form of the redox mediator and being in sufficient amount to insure that current produced by diffusion limited electroreduction is limited by the reduction of the oxidized form of the redox mediator at the working electrode surface, the enzyme being of sufficient type and in sufficient amount to catalyze the reaction involving enzyme, analyte, and the reduced form of the redox mediator, and the buffer having a lower reduction potential than the oxidized form of the redox mediator and being of sufficient type and in sufficient amount to provide and maintain a pH at which the enzyme catalyzes the reaction involving enzyme, analyte, and the reduced form of the redox mediator.

37. The device of claim 36, wherein the reagent further comprises
a microcrystalline material of sufficient type and in sufficient amount to disperse the redox mediator in the reagent,
a surfactant of sufficient type and in sufficient amount to wet a sample containing the analyte, and
a reagent stabilizer of sufficient type and in sufficient amount to stabilize the reagent.

38. The device of claim 36, further comprising:
e. a power source in electrical connection with the working and counter electrodes and capable of supplying an electrical potential difference between the working and counter electrodes sufficient to cause diffusion limited electroreduction of the oxidized form of the redox mediator at the surface of the working electrode; and
f. a meter in electrical connection with the working and counter electrodes and capable of measuring the diffusion limited current produced by the reduction of the oxidized form of the redox mediator at the working electrode surface.

* * * * *